United States Patent
Mitsui et al.

(10) Patent No.: US 6,235,222 B1
(45) Date of Patent: May 22, 2001

(54) METHOD FOR MANUFACTURING FLUOROARYL MAGNESIUM HALIDE

(75) Inventors: Hitoshi Mitsui, Kitakatsuragi-gun; Toshiya Iida, Suita; Ikuyo Ikeno, Osaka; Naoko Hirano, Nishinomiya; Yukiko Ariyoshi, Yamatokoriyama, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/425,385

(22) Filed: Oct. 22, 1999

(30) Foreign Application Priority Data

Oct. 23, 1998 (JP) ................................... 10-302832

(51) Int. Cl.$^7$ ....................................... C07F 3/02
(52) U.S. Cl. .................. 260/665 G; 568/1; 558/287; 558/294; 558/295
(58) Field of Search .............. 260/665 G; 558/287, 558/294, 295; 568/1

(56) References Cited

U.S. PATENT DOCUMENTS 5,693,261  12/1997  Krzystowczyk et al. ............ 260/665

FOREIGN PATENT DOCUMENTS 9-295985  11/1997  (JP) .

OTHER PUBLICATIONS

"Aromatic Polyfluoro–compounds. Part I. The Synthesis of Aromatic Polyfluoro–compounds from Pentafluorobenzene." E. Nield, et al., J. Chem. Soc., pp. 166–171, 1959.
"Synthesis of Some Pentafluorophenylmagnesium Compounds." William L. Respess, et al. J. Organometal. Chem., 11(1968), pp. 619–622.
"Synthesis of Polyfluoroaromatic Magnesium Compounds Through the Exchange Reaction." Christ Tamborski, et al. J. Organometal. Chem., 26(1971), pp. 153–156.

*Primary Examiner*—Paul F. Shaver
(74) *Attorney, Agent, or Firm*—Dike, Bronstein, Roberts & Cushman, LLP; David G. Conlin

(57) ABSTRACT

In order to provide a method of safely, efficiently, and industrially manufacturing fluoroaryl magnesium halide containing no impurities, such as coloring components, by a relatively gradual reaction compared with the conventional reactions, and a method of readily and efficiently manufacturing a highly-pure fluoroaryl borane derivative, fluoroaryl magnesium halide expressed by General Formula (1):

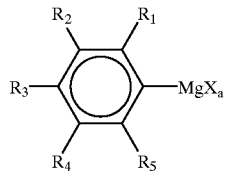

(1)

where each of $R_1$–$R_5$ independently represents H, F, a hydrocarbon group, or an alkoxy group, provided that at least three of $R_1$–$R_5$ are fluorine atoms, and $X_a$ represents Cl, Br, or I;

is manufactured by reacting, in a solvent containing a chain ether solvent, hydrocarbon magnesium halide expressed by General Formula (2):

$$R_6 MgX_a \qquad (2)$$

where $R_6$ represents a hydrocarbon group, and $X_a$ represents Cl, Br, or I;

with fluoroaryl halide expressed by General Formula (3):

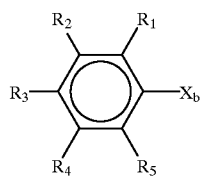

(3)

where each of $R_1$–$R_5$ independently represents H, F, a hydrocarbon group, or an alkoxy group, provided that at least three of $R_1$–$R_5$ are fluorine atoms and $X_b$ represents Br or I.

19 Claims, No Drawings

METHOD FOR MANUFACTURING FLUOROARYL MAGNESIUM HALIDE

FIELD OF THE INVENTION

The present invention relates to a method for manufacturing fluoroaryl magnesium halide which is a useful compound as a Grignard reagent used in various types of organic synthetic reactions. The present invention also relates to a method for manufacturing a fluoroaryl borane derivative which is a useful compound as a cocatalyst for a metallocene catalyst (polymerization catalyst) used in a cation complex polymerization reaction or a catalyst for silicone photo-polymerization, for example.

BACKGROUND OF THE INVENTION

Fluoroaryl magnesium halide is a useful compound as a Grignard reagent used in various types of organic synthetic reactions, for example. Also, the fluoroaryl magnesium halide is a useful compound, for example, as an intermediate of a fluoroaryl borane derivative, used in manufacturing a cocatalyst which promotes an activity of a metallocene catalyst (polymerization catalyst) used in a cation complex polymerization reaction, or a catalyst for silicone photo-polymerization. Recently, the metallocene catalyst has been receiving considerable attention as a polyolefin polymerization catalyst.

Various proposals have been made as a method of synthesizing the fluoroaryl magnesium halide. For example, J. Chem. Soc., 166 (1959) discloses a method of synthesizing pentafluorophenyl magnesium bromide, which is a species compound of the fluoroaryl magnesium halide, by reacting bromopentafluorobenzene with magnesium using diethyl ether as a solvent.

Also, J. Organometal. Chem., 11, 619–622 (1968) and J. Organometal. Chem., 26, 153–156 (1971) disclose a method of synthesizing pentafluorophenyl magnesium halide, which is a species compound of the fluoroaryl magnesium halide, by a Grignard exchange reaction of fluoroaryl halide (chloropentafluorobenzene, bromopentafluorobenzene, and iodopentafluorobenzene) and ethyl magnesium halide using tetrahydrofuran (THF) as a solvent. Also, U.S. Pat. No. 5,693,261 discloses a method of synthesizing pentafluorophenyl magnesium halide by a Grignard exchange reaction of chloropentafluorobenzene and isopropyl magnesium halide.

On the other hand, Japanese Laid-open Patent Application No. 295985/1997 (Japanese Official Gazette, Tokukaihei No. 9-295985, published on Nov. 18, 1997) discloses a method of preparing fluoroaryl magnesium halide (Grignard reagent) by reacting fluoroaryl halide with magnesium using alkyl halide as a catalyst.

However, in the method of synthesizing pentafluorophenyl magnesium bromide disclosed in J. Chem. Soc., 166 (1959) supra, the synthesis pentafluorophenyl magnesium bromide is colored considerably with coloring components produced by the side reaction or the like. For this reason, when a fluoroaryl borane derivative is synthesized by using the pentafluorophenyl magnesium bromide as a Grignard reagent, a colored fluoroaryl borane derivative is produced as the final product unless the coloring components are removed.

The method for manufacturing pentafluorophenyl magnesium halide disclosed in J. Organometal. Chem., 11, 619–622 (1968) and J. Organometal. Chem., 26, 153–156 (1971) supra use THF as the solvent. However, the fluoroaryl borane derivative synthesized using a THF solution of the resulting pentafluorophenyl magnesium halide includes strong Lewis acids, for example. Thus, there is a problem that the resulting fluoroaryl borane derivatives trigger ring-opening polymerization of THF used as the solvent or causes a large amount of by-product to be produced.

Also, the method for manufacturing pentafluorophenyl magnesium halide disclosed in U.S. Pat. No. 5,693,261 supra has a problem that, because chloropentafluorobenzene has poor reactivity, chloropentafluorobenzene has to be used excessively with respect to isopropyl magnesium halide. Further, this method has another problem that it demands a step of removing the excessively used chloropentafluorobenzene from the final product (commercial goods).

The method of preparing the Grignard reagent disclosed in Japanese Laid-open Patent Application No. 295985/1997 supra has a problem that, although the coloring of the resulting Grignard reagent is slightly reduced if diethyl ether is used as the solvent (reaction solvent), the resulting Grignard reagent is still colored black. Also, the reaction hardly proceeds if any other kind of ether solvents is used.

Generally, diethyl ether is used as a solvent when preparing the Grignard reagent from fluoroaryl halide and magnesium. However, reaction heat produced in the reaction of bromopentafluorobenzene and magnesium is so large (89 Kcal/mol) that the reaction is not readily controlled. Particularly, diethyl ether involves a safety problem because it is a highly inflammable compound with a low boiling point.

SUMMARY OF THE INVENTION

The present invention is devised to solve the above problems and has an object to provide a method of safely, efficiently, and industrially manufacturing fluoroaryl magnesium halide containing no impurities, such as coloring components, by a relatively gradual reaction compared with the conventional reactions. The present invention has another object to provide a method of readily and efficiently manufacturing a fluoroaryl borane derivative at high purity, which is a useful compound as a cocatalyst for a metallocene catalyst or a catalyst for silicone photo-polymerization.

The inventors of the present invention conducted an assiduous study of the method for manufacturing the fluoroaryl magnesium halide and the method for manufacturing the fluoroaryl borane derivative. In due course, the inventors discovered that, by conducting a Grignard exchange reaction of hydrocarbon magnesium halide and fluoroaryl halide in a solvent containing a chain ether solvent, fluoroaryl magnesium halide containing no impurities, such as coloring components, can be manufactured safely, efficiently, and industrially by a relatively gradual reaction compared with conventional reactions. Also, the inventors discovered that the reaction proceeds particularly in a preferable manner in a solvent containing an ether solvent other than diethyl ether. Further, the inventors achieved the present invention when they discovered that, by reacting the fluoroaryl magnesium halide obtained by the above method with a boron compound, a highly-pure fluoroaryl borane derivative containing no impurities, such as coloring components, can be manufactured readily and efficiently.

More specifically, in order to solve the above problems, a method for manufacturing fluoroaryl magnesium halide of the present invention is a method for manufacturing fluoroaryl magnesium halide expressed by General Formula (1):

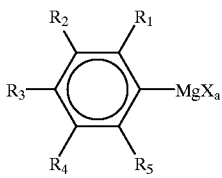

(1)

where each of $R_1$, $R_2$, $R_3$, $R_4$, and $R_5$ independently represents a hydrogen atom, a fluorine atom, a hydrocarbon group, or an alkoxy group, provided that at least three of $R_1$–$R_5$ are fluorine atoms, and $X_a$ represents a chlorine atom, a bromine atom, or an iodine atom;

by reacting, in a solvent containing a chain ether solvent, hydrocarbon magnesium halide expressed by General Formula (2):

$$R_6MgX_a \qquad (2)$$

where $R_6$ represents a hydrocarbon group, $X_a$ represents a chlorine atom, a bromine atom, or an iodine atom;

with fluoroaryl halide expressed by General Formula (3):

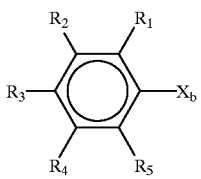

(3)

where each of $R_1$, $R_2$, $R_3$, $R_4$, and $R_5$ independently represents a hydrogen atom, a fluorine atom, a hydrocarbon group, or an alkoxy group, provided that at least three of $R_1$–$R_5$ are fluorine atoms, and $X_b$ represents a bromine atom or an iodine atom.

In order to solve the above problems, a method for manufacturing tris(fluoroaryl)borane of the present invention is a method for manufacturing tris(fluoroaryl)borane expressed by General Formula (5):

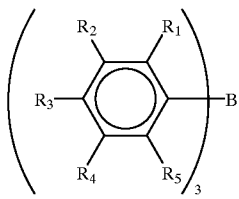

(5)

where each of $R_1$, $R_2$, $R_3$, $R_4$, and $R_5$ independently represents a hydrogen atom, a fluorine atom, a hydrocarbon group, or an alkoxy group, provided that at least three of $R_1$–$R_5$ are fluorine atoms;

by reacting the fluoroaryl magnesium halide manufactured by the above method with a boron compound expressed by General Formula (4):

$$B(X_c)_3 \qquad (4)$$

where $X_c$ represents a fluorine atom, a chlorine atom, a bromine atom, an iodine atom, or an alkoxy group.

Further, in order to solve the above problems, a method for manufacturing a tetrakis(fluoroaryl) borate·magnesium compound of the present invention is a method for manufacturing a tetrakis(fluoroaryl) borate·magnesium compound expressed by General Formula (6):

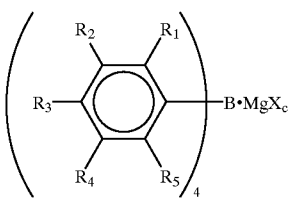

(6)

where each of $R_1$, $R_2$, $R_3$, $R_4$, and $R_5$ independently represents a hydrogen atom, a fluorine atom, a hydrocarbon group, or an alkoxy group, provided that at least three of $R_1$–$R_5$ are fluorine atoms, and $X_c$ represents a fluorine atom, a chlorine atom, a bromine atom, an iodine atom, or an alkoxy group;

by reacting the fluoroaryl magnesium halide obtained by the above method with the boron compound expressed by General Formula (4) above.

Furthermore, in order to solve the above problems, a method for manufacturing a fluoroaryl borate·magnesium halide derivative of the present invention is a method of manufacturing a fluoroaryl borate·magnesium halide derivative expressed by General Formula (8):

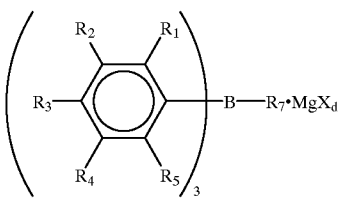

(8)

where each of $R_1$, $R_2$, $R_3$, $R_4$, and $R_5$ independently represents a hydrogen atom, a fluorine atom, a hydrocarbon group, or an alkoxy group, provided that at least three of $R_1$–$R_5$ are fluorine atoms, $R_7$ represents a hydrocarbon group, and $X_d$ represents a chlorine atom, a bromine atom, or an iodine atom;

by reacting the tris(fluoroaryl)borane obtained by the above method with hydrocarbon magnesium halide expressed by General Formula (7):

$$R_7MgX_d \qquad (7)$$

where $R_7$ represents a hydrocarbon group, $X_d$ represents a chlorine atom, a bromine atom, or an iodine atom.

Further objects, the nature and advantages of the invention will be understood by the following description. Also, the effects of the present invention will be explained clearly in the following description.

DESCRIPTION OF THE EMBODIMENTS

A method for manufacturing the fluoroaryl magnesium halide expressed by General Formula (1) above of the present invention is a method of reacting the hydrocarbon magnesium halide expressed by General Formula (2) above (hereinafter, referred to as hydrocarbon magnesium halide (2)) with the fluoroaryl halide expressed by General Formula (3) above by a Grignard exchange reaction. The resulting fluoroaryl magnesium halide is a suitable compound as an intermediate in manufacturing a fluoroaryl borane derivative.

Examples of the fluoroaryl borane derivative to be manufactured in the present invention include: the tris(fluoroaryl) borane expressed by General Formula (5) above; the tetrakis (fluoroaryl)borate.magnesium compound expressed by General Formula (6) above; and the fluoroaryl borate.magnesium halide derivative expressed by General Formula (8) above.

Thus, each of the method for manufacturing the tris (fluoroaryl)borane expressed by General Formula (5) above and the method for manufacturing the tetrakis(fluoroaryl) borate.magnesium compound expressed by General Formula (6) above, presented as the method for manufacturing the fluoroaryl borane derivative of the present invention, is a method of reacting the fluoroaryl magnesium halide obtained by the above method with the boron compound expressed by General Formula (4) above. Also, the method for manufacturing the fluoroaryl borate.magnesium halide derivative expressed by General Formula (8) above, presented as the method for manufacturing the fluoroaryl borane derivative of the present invention, is a method of reacting the tris(fluoroaryl)borane with the hydrocarbon magnesium halide expressed by General Formula (7) above (hereinafter, referred to as hydrocarbon magnesium halide (7)).

The fluoroaryl magnesium halide to be manufactured in the present invention is a compound whose substituent groups denoted as $R_1$ through $R_5$ in General Formula (1) above are independently a hydrogen atom, a fluorine atom, a hydrocarbon group, or an alkoxy group, provided that at least three of $R_1$–$R_5$ are fluorine atoms, and whose substituent group denoted as $X_a$ is a chlorine atom, a bromine atom, or an iodine atom.

Also, the fluoroaryl borane derivative to be manufactured in the present invention is a compound whose substituent groups denoted as $R_1$ through $R_5$ in General Formulas (5), (6), and (8) above are independently a hydrogen atom, a fluorine atom, a hydrocarbon group, or an alkoxy group, provided that at least three of $R_1$–$R_5$ are fluorine atoms. In addition, a substituent group denoted as $X_c$ in General Formula (6) above is a fluorine atom, a chlorine atom, a bromine atom, an iodine atom or an alkylalkoxy group. On the other hand, a substituent group denoted as $R_7$ in General Formula (8) above is a hydrocarbon group, and a substituent group denoted as $X_d$ is a chlorine atom, a bromine atom, or an iodine atom.

Examples of the hydrocarbon group include an aryl group, a straight-chain, branched-chain or cyclic alkyl group having up to 12 carbon atoms, and a straight-chain, branched-chain or cyclic alkenyl group having 2 to 12 carbon atoms. The hydrocarbon group may further include a functional group (inactive functional group) having atoms inactive to the reactions taking place in the present invention, such as a fluorine atom, an oxygen atom, a sulfur atom, and a nitrogen atom. Examples of such a functional group include a methoxy group, a methylthio group, an N,N-dimethylamino group, an o-anise group, a p-anise group, a trimethylsilyloxy group, a dimethyl-t-butylsilyloxy group, a trifluoromethyl group, etc.

The alkoxy group is expressed by General Formula (A):

—OR$_a$ (A)

where $R_a$ represents a hydrocarbon group. Examples of the hydrocarbon group denoted as $R_a$ in General Formula (A) include an aryl group, a straight-chain, branched-chain, cyclic alkyl group having up to 12 carbon atoms, or a straight-chain, branched-chain, cyclic alkenyl group having 2 to 12 carbon atoms. The hydrocarbon group may further include a functional group inactive to the reactions taking place in the present invention.

Examples of the alkoxy group expressed by General Formula (A) above include: a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, a phenoxy group, etc.

Also, examples of the alkylalkoxy group are alkoxy groups, including a straight-chain, branched-chain, or cyclic alkyl group having up to 12 carbons. The alkylalkoxy group may further include a functional group inactive to the reactions taking place in the present invention.

The following description will describe in detail a method for manufacturing fluoroaryl magnesium halide of the present invention.

Examples of the fluoroaryl halide expressed by General Formula (3) above include: bromopentafluorobenzene, iodopentafluorobenzene, 1-bromo-2,3,4,5-tetrafluorobenzene, 1-bromo-2,3,4,6-tetrafluorobenzene, 1-bromo-2,3,5,6-tetrafluorobenzene, 1-iodo-2,3,4,5-tetrafluorobenzene, 1-iodo-2,3,4,6-tetrafluorobenzene, 1-iodo-2,3,5,6-tetrafluorobenzene, 1-bromo-2,3,4-trifluorobenzene, 1-bromo-2,3,5-trifluorobenzene, 1-bromo-2,4,5-trifluorobenzene, 1-bromo-2,4,6-trifluorobenzene, 1-bromo-3,4,5-trifluorobenzene, 1-iodo-2,3,4-trifluorobenzene, 1-iodo-2,3,5,-trifluorobenzene, 1-iodo-2,4,5-trifluorobenzene, 1-iodo-2,4,6-trifluorobenzene, 1-iodo-3,4,5-trifluorobenzene, etc.

It should be noted that fluoroaryl halide, in which at least three of the substituent groups denoted as $R_1$–$R_5$ in General Formula (3) above are not fluorine atoms, does not undergo the Grignard exchange reaction with the hydrocarbon magnesium halide (2).

Examples of hydrocarbon magnesium halide (2) include: phenyl magnesium chloride, phenyl magnesium bromide, phenyl magnesium iodide, methyl magnesium chloride, methyl magnesium bromide, methyl magnesium iodide, ethyl magnesium chloride, ethyl magnesium bromide, ethyl magnesium iodide, n-propyl magnesium chloride, n-propyl magnesium bromide, n-propyl magnesium iodide, isopropyl magnesium chloride, isopropyl magnesium bromide, isopropyl magnesium iodide, n-butyl magnesium chloride, n-butyl magnesium bromide, n-butyl magnesium iodide, allyl magnesium chloride, allyl magnesium bromide, allyl magnesium iodide, cyclohexyl magnesium chloride, cyclohexyl magnesium bromide, cyclohexyl magnesium iodide, etc.

Of all these examples of the hydrocarbon magnesium halide (2), particularly preferable are: phenyl magnesium chloride, phenyl magnesium bromide, phenyl magnesium iodide, ethyl magnesium chloride, ethyl magnesium bromide, ethyl magnesium iodide, n-propyl magnesium chloride, n-propyl magnesium bromide, n-propyl magnesium iodide, isopropyl magnesium chloride, isopropyl magnesium bromide, isopropyl magnesium iodide, allyl magnesium chloride, allyl magnesium bromide, allyl magnesium iodide, cyclohexyl magnesium chloride, cyclohexyl magnesium bromide, and cyclohexyl magnesium iodide.

A ratio of the hydrocarbon magnesium halide (2) to the fluoroaryl halide is not especially limited. However, in case that the fluoroaryl magnesium halide is manufactured to selectively manufacture tris(fluoroaryl)borane, the ratio is preferably in a range between 0.8 and 2.0 equivalents, and more preferably in a range between 0.9 and 1.5 equivalent. When the ratio is less than 0.8 equivalent, a large amount of unreacted fluoroaryl halide may remain in the tris (fluoroaryl)borane obtained as the final product. It is difficult to remove the fluoroaryl magnesium halide from the final product, and the final product may lose a commercial value. When the ratio exceeds 2.0 equivalents, a large amount of unreacted hydrocarbon magnesium halide (2) may remain in the final product.

On the other hand, in case that the fluoroaryl magnesium halide is manufactured to selectively manufacture the tetrakis(fluoroaryl)borate.magnesium compound, the ratio is preferably in a range between 0.8 and 2.0 equivalents, and more preferably in a range between 0.9 and 1.5 equivalent. When the ratio is less than 0.8 equivalent, the yield of the tetrakis (fluoroaryl)borate.magnesium compound as the final product may be lowered. When the ratio exceeds 2.0 equivalents, a large amount of unreacted hydrocarbon magnesium halide (2) may remain in the final product. It is time-consuming to remove the unreacted compounds from the final product. Therefore, in order to use the fluoroaryl halide in the following step without leaving any unreacted fluoroaryl halide nor causing a problem of removing the unreacted hydrocarbon magnesium halide (2) therefrom, the reaction is conducted by setting the ratio of the hydrocarbon magnesium halide (2) to the fluoroaryl halide to be in a range between 1 and 1.2 equivalent.

The reaction of the hydrocarbon magnesium halide (2) with the fluoroaryl halide is conducted in a solvent containing a chain ether solvent. The solvent containing the chain ether solvent is not especially limited as long as it is a liquid compound which remains inactive to the reactions taking place in the present invention, and in which the fluoroaryl halide and hydrocarbon magnesium halide (2) can be dissolved or suspended.

Examples of the chain ether solvent include aliphatic ether solvents, such as diethyl ether, dipropyl ether, diisopropyl ether, dibutyl ether, t-butyl methyl ether, diisoamyl ether, 1,2-dimethoxyethane, and 1,2-diethoxyethane. One member or a mixture of two or more members selected from these examples can be effectively used.

Further, these examples of the chain ether solvent may be in the form of a mixed solvent with solvents of the other kinds, including:

an aliphatic hydrocarbon solvent, such as pentane, hexane, and heptane;

an alicyclic hydrocarbon solvent, such as cyclopentane, cyclohexane, and methyl cyclohexane;

an aromatic hydrocarbon solvent, such as benzene, toluene, xylene, and anisole; etc.

Also, the chain ether solvent can be mixed with a cyclic ether, such as tetrahydrofuran, to the extent that ring-opening polymerization and production of a by-product are inhibited. The chain ether solvent can be mixed with one member or a mixture of two or more members selected from the foregoing solvents of the other kinds. The solvent referred to hereinafter means a solvent containing the chain ether solvent unless otherwise specified.

Compared with conventional reactions (for example, a reaction of bromopentafluorobenzene and magnesium), a reaction of the fluoroaryl halide and hydrocarbon magnesium halide (2) yields small reaction heat, and therefore, proceeds gradually. Thus, in the method for manufacturing the fluoroaryl magnesium halide of the present invention, the reaction can be readily controlled and conducted smoothly in the solvent. Hence, a mixed solvent of the chain ether solvent and another solvent having a higher boiling point than the chain ether solvent can be used, for example, thereby making it possible to conduct the reaction more safely.

A ratio (concentration) of the chain ether solvent to the solvent containing the same is not especially limited as long as the reaction can proceed smoothly. However, the ratio is preferably 1.0 wt % or greater, more preferably 5.0 wt % or greater, and most preferably 10.0 wt % or greater. When the ratio is less than 1.0 wt %, the efficiency of the reaction becomes poor because of an increased amount of the solvent, and the reaction rate may become extremely slow.

An amount of used solvent is not especially limited as long as the fluoroaryl halide and hydrocarbon magnesium halide (2) can be dissolved or suspended therein and the reaction can proceed smoothly. However, the amount is such that a concentration of the synthesis fluoroaryl magnesium halide in the reaction solution is preferably in a range between 0.1 and 80 wt %, more preferably in a range between 1.0 and 70 wt %, and most preferably in a range between 5.0 and 60 wt %. When the concentration is less than 0.1 wt %, the efficiency of the reaction becomes poor because of an increased amount of the solvent, and the reaction rate may become extremely slow. When the concentration exceeds 80 wt %, the fluoroaryl magnesium halide may precipitate in the solution and become difficult to handle.

The method of mixing the fluoroaryl halide with the hydrocarbon magnesium halide (2) is not especially limited. For example, a solution of the hydrocarbon magnesium halide (2) can be dropped to the fluoroaryl halide or a solution thereof, or the fluoroaryl halide or a solution thereof can be dropped to a solution of the hydrocarbon magnesium halide (2). Further, the fluoroaryl halide or a solution thereof and a solution of the hydrocarbon magnesium halide (2) can be dropped to the solvent.

The reaction temperature of the above reaction is not especially limited. However, the reaction temperature is preferably at or above −30° C. and at or below the refluxing temperature of the solvent, more preferably at or above −20° C. and at or below 200° C. or the refluxing temperature, whichever is the lower, and most preferably at or above −10° C. and at or below 100° C. or the refluxing temperature, whichever is the lower.

The reaction time and pressure of the above reaction are not especially limited, and can be set arbitrary in such a manner so as to complete the reaction depending on the other conditions, including the reaction temperature, an amount of the hydrocarbon magnesium halide (2), an amount of the fluoroaryl halide, a combination of these compounds, the composition of the solvent, etc. Thus, the reaction is conducted under any of a normal pressure, an applied pressure or a reduced pressure. Further, the reaction is preferably conducted under an inert gas atmosphere, such as a nitrogen gas.

By conducting the Grignard exchange reaction, the fluoroaryl magnesium halide expressed by General Formula (1) above is manufactured. The fluoroaryl magnesium halide manufactured by the above reaction is a useful compound used as a Grignard reagent or the like used in various types of organic synthesis reactions. For example, the fluoroaryl magnesium halide is used as an intermediate in producing a fluoroaryl borane derivative which will be described below.

In case that the fluoroaryl magnesium halide used as the intermediate is colored by coloring components produced as impurities by a side-reaction or the like, the resulting fluoroaryl borane derivative is also colored by the coloring components.

However, according to the method for manufacturing the present invention, the fluoroaryl magnesium halide can be synthesized by a gradual reaction which yields small reaction heat, and therefore, no impurities, such as the coloring components, are not produced. Thus, the above manufacturing method can provide fluoroaryl magnesium halide useful as the Grignard reagent or the like used in various types of organic synthesis reactions.

By the method for manufacturing the fluoroaryl magnesium halide of the present invention, not only the fluoroaryl magnesium halide as the target product, but also alkyl halide is produced. However, the alkyl halide does not give any adverse effect to the performance of the fluoroaryl magnesium halide used as the Grignard reagent. Hence, it is not necessary to remove the alkyl halide before the fluoroaryl borane derivative is manufactured using the fluoroaryl magnesium halide. For instance, the alkyl halide can be distilled out with the solvent by heating while the fluoroaryl borane derivative is manufactured.

Next, the following will describe in detail the method for manufacturing tris(fluoroaryl)borane and a tetrakis(fluoroaryl)borate.magnesium compound, which are species compounds of the fluoroaryl borane derivative of the present invention.

Examples of the boron compound expressed by General Formula (4) above include: boron trifluoride, boron trichloride, boron tribromide, boron triiodide, trimethoxy boron, etc. These examples of the boron compound may form a complex with diethyl ether or tetrahydrofuran, etc.

A mole ratio of the fluoroaryl magnesium halide expressed by General Formula (1) above and the boron compound (fluoroaryl magnesium halide/boron compound) is not especially limited. However, the mole ratio is preferably in a range between 1.0 and 5.0. In case that the tris(fluoroaryl)borane expressed by General Formula (5) above is selectively manufactured as the fluoroaryl borane derivative, the mole ratio is more preferably in a range between 2.0 and 3.4, and most preferably in a range between 2.5 and 3.3. On the other hand, in case that the tetrakis(fluoroaryl)borate.magnesium compound expressed by General Formula (6) above is selectively manufactured as the fluoroaryl borane derivative, the mole ratio is more preferably in a range between 3.5 and 5.0, and most preferably in a range between 3.7 and 4.5.

The reaction of the fluoroaryl magnesium halide and boron compound is conducted by mixing the boron compound or a solution thereof with a solution (reaction solution) of the fluoroaryl magnesium halide obtained by synthesizing the fluoroaryl magnesium halide. In other words, the reaction is conducted in the solvent used in manufacturing the fluoroaryl magnesium halide. From the view point of safety alone, a solvent containing the chain ether solvent except for diethyl ether is used preferably as the solvent in general. In this case, however, the following problems may arise with the reaction of the fluoroaryl magnesium halide and boron compound:

(1) the reaction rate may be extremely slow;
(2) the yield of the trisfluoroaryl borane or tetrakis(fluoroaryl)borate.magnesium compound is reduced by a side-reaction.

Nevertheless, the reaction activity can be upgraded by conducting the reaction in the presence of 0.5–3.0 equivalents of diethyl ether (it may be in the form of a complex with the boron compound) with respect to the fluoroaryl magnesium halide.

An amount of used solvent is not especially limited as long as the fluoroaryl magnesium halide and boron compound can be dissolved or suspended therein and the reaction can proceed smoothly. Also, in case that the boron compound is mixed in the form of a solution, the solvent used to produce the solution is of the same or different compound used in manufacturing the fluoroaryl magnesium halide. Further, the reaction solution can be diluted with addition of the solvent, or the solvent exchange can be conducted by adding a solvent different from the one used for the reaction and then distilling out the one used for the reaction, as the case may be.

The method of mixing a solution of the fluoroaryl magnesium halide with the boron compound is not especially limited. For example, in case that the tris(fluoroaryl)borane is manufactured selectively, it is preferable to drop a solution of the fluoroaryl magnesium halide to the boron compound or a solution thereof. On the other hand, in case that the tetrakis(fluoroaryl)borate.magnesium compound is selectively manufactured, the boron compound or a solution thereof may be dropped to a solution of the fluoroaryl magnesium halide, or a solution of the fluoroaryl magnesium halide may be dropped to the boron compound or a solution thereof. Further, a solution of the fluoroaryl magnesium halide and the boron compound or a solution thereof may be added to the solvent.

The mixing temperature at which a solution of the fluoroaryl magnesium halide is mixed with the boron compound is preferably in a range between −30° C. and 50° C., and more preferably in a range between −10° C. and 40° C. in case that the tris(fluoroaryl)borane is selectively manufactured. If the mixing temperature is below −30° C., the reaction rate may become extremely slow, and if the mixing temperature exceeds 50° C., the tetrakis(fluoroaryl)borate.magnesium compound may be yielded as a by-product. On the other hand, in case that the tetrakis(fluoroaryl)borate.magnesium compound is selectively manufactured, the mixing temperature is preferably at or above −30° C. and at or below the refluxing temperature of the solvent, and more preferably at or above −20° C. and at or below 200° C. or the refluxing temperature, whichever is the lower, and most preferably at or above −10° C. and at or below 150° C. or the refluxing temperature, whichever is the lower.

The reaction temperature of the above reaction is not especially limited. However, the reaction temperature is preferably at or above −30° C. and at or below the refluxing temperature of the solvent. For example, in case that the tris(fluoroaryl)borane is manufactured selectively, the reaction temperature is more preferably at or above −20° C. and at or below 150° C. or the refluxing temperature, whichever is the lower, and most preferably at or above −10° C. and at or below 100° C. or the refluxing temperature, whichever is the lower. If the reaction temperature is below −30° C., the reaction rate may become extremely slow. On the other hand, if the reaction temperature exceeds 150° C. (or the refluxing temperature), the tris(fluoroaryl)borane may decompose. In case that the tetrakis(fluoroaryl)borate.magnesium compound is manufactured selectively, the reaction temperature is more preferably at or above 0° C. and at or below 200° C. or the refluxing temperature, whichever is the lower, and most preferably at or above 30° C. and at or below 150° C. or the refluxing temperature, whichever is the lower. If the reaction temperature is below −30° C., the reaction rate may become extremely slow. On the other hand, if the reaction temperature exceeds 200° C. (or the refluxing temperature), the tetrakis(fluoroaryl)borate.magnesium compound may decompose.

The reaction time and pressure of the above reaction are not especially limited, and can be set in such a manner so as to complete the reaction depending on the other reaction conditions, including the reaction temperature, an amount of the fluoroaryl magnesium halide, an amount of the boron compound, a combination of these compounds, the composition of the solvent, etc. Hence, the reaction is conducted under any of a normal pressure, an applied pressure, or a reduced pressure. Further, the reaction is preferably conducted under an inert gas atmosphere, such as a nitrogen gas. Furthermore, the solvent and/or the alkyl halide produced as a by-product when the fluoroaryl magnesium halide was produced can be distilled out during or after the reaction, as the case may be. Alternately, the solvent exchange can be conducted during or after the reaction.

By conducting the Grignard reaction, either the tris (fluoroaryl)borane expressed by General Formula (5) above or the tetrakis(fluoroaryl)borate.magnesium compound expressed by General Formula (6) above is selectively manufactured. The method for manufacturing the present invention can manufacture tris(fluoroaryl)borane and a tetrakis(fluoroaryl) borate.magnesium compound containing no impurities, such as coloring components.

Next, the following will explain in detail the method for manufacturing the fluoroaryl borate.magnesium halide derivative as the fluoroaryl borane derivative of the present invention.

Examples of the hydrocarbon magnesium halide (7) include: besides the compounds specified as examples of the hydrocarbon magnesium halide (2), p-fluorophenyl magnesium bromide, 2,6-difluorophenyl magnesium bromide, 2,4, 6-trifluorophenyl magnesium bromide, 2,3,5,6-tetrafluorophenyl magnesium bromide, etc.

A ratio of the hydrocarbon magnesium halide (7) to the tris(fluoroaryl)borane expressed by General Formula (5) above is not especially limited. However, the ratio is preferably 0.5 equivalent or greater, more preferably in a range between 0.5 and 5.0 equivalents, and most preferably in a range between 1.0 and 3.0 equivalents. If the ratio is smaller than 0.5 equivalents, a large amount of the tris(fluoroaryl) borane may remain unreacted. If the ratio exceeds 5.0 equivalents, a large amount of the hydrocarbon magnesium halide (7) may remain unreacted. It is time-consuming to remove these unreacted compounds.

The reaction of the tris(fluoroaryl)borane and hydrocarbon magnesium halide (7) is conducted by mixing a solution of the hydrocarbon magnesium halide (7) with a solution (reaction solution) of the tris(fluoroaryl)borane obtained by synthesizing the tris(fluoroaryl)borane. In other words, the reaction is conducted in the solvent used in manufacturing the tris(fluoroaryl)borane. From the view point of safety alone, a solvent containing the chain ether solvent except for diethyl ether is used preferably as the solvent in general. In this case, however, the following problems may arise with the reaction of the tris(fluoroaryl)borane and the hydrocarbon magnesium halide (7):

(1) the reaction rate may be extremely slow;
(2) the yield of the fluoroaryl borate.magnesium compound may be lowered by a side-reaction.

Nevertheless, the reaction activity can be upgraded by conducting the reaction in the presence of 0.5–3.0 equivalents of diethyl ether (it may be in the form of a complex with the (fluoroaryl)borane) with respect to the tris (fluoroaryl)borane.

An amount of used solvent is not especially limited as long as the tris(fluoroaryl)borane and hydrocarbon magnesium halide (7) can be dissolved or suspended therein and the reaction can proceed smoothly. Also, for example, the solvent used in producing a solution of the hydrocarbon magnesium halide (7) may be of the same or different compound used in manufacturing the tris(fluoroaryl)borane. Further, the reaction solution can be diluted with addition of the solvent, or the solvent exchange can be conducted by adding a solvent different from the one used for the reaction and then distilling out the one used for the reaction, as the case may be.

The method of mixing a solution of the tris(fluoroaryl) borane and a solution of the hydrocarbon magnesium halide (7) is not especially limited. For example, the solution of the hydrocarbon magnesium halide (7) may be dropped to the solution of the tris(fluoroaryl)borane, or the solution of the tris(fluoroaryl)borane may be dropped to the solution of the hydrocarbon magnesium halide (7). Further, the solution of the tris(fluoroaryl)borane and the solution of the hydrocarbon magnesium halide (7) may be dropped to the solvent.

The mixing temperature at which the solution of the tris(fluoroaryl)borane and the solution of the hydrocarbon magnesium halide (7) is not especially limited. However, the mixing temperature is preferably at or above $-30°$ C. and at or below the refluxing temperature of the solvent, and more preferably at or above $-20°$ C. and at or below $200°$ C. or the refluxing temperature, whichever is the lower, and most preferably at or above $-10°$ C. and at or below $150°$ C. or the refluxing temperature, whichever is the lower.

The reaction temperature of the above reaction is not especially limited. However, the reaction temperature is preferably at or above $-30°$ C. and at or below the refluxing temperature of the solvent, more preferably at or above $0°$ C. and at or below $200°$ C. or the refluxing temperature, whichever is the lower, and most preferably at or above $30°$ C. and at or below $150°$ C. or the refluxing temperature, whichever is the lower. If the reaction temperature is below $-30°$ C., the reaction rate may become extremely slow. On the other hand, if the reaction temperature exceeds $200°$ C. (or the refluxing temperature), the fluoroaryl borate.magnesium halide derivative may decompose.

The reaction time and pressure of the above reaction are not especially limited, and can be set in such a manner so as to complete the reaction depending on the other reaction conditions, including the reaction temperature, an amount of the tris(fluoroaryl)borane, an amount of the hydrocarbon magnesium halide (7), a combination of these compounds, the composition of the solvent, etc. Hence, the reaction is conducted under any of a normal pressure, an applied pressure, or a reduced pressure. Further, the reaction is preferably conducted under an inert gas atmosphere, such as a nitrogen gas. Furthermore, the solvent and/or the alkyl halide produced as a by-product when the fluoroaryl magnesium halide was produced can be distilled out during or after the reaction, as the case may be. Alternately, the solvent exchange can be conducted during or after the reaction.

By conducting the Grignard reaction, the fluoroaryl borate.magnesium halide derivative expressed by General Formula (8) above is manufactured. The method for manufacturing the present invention can manufacture a fluoroaryl borate.magnesium halide derivative containing no impurities, such as coloring components.

According to the method for manufacturing the fluoroaryl borane derivative of the present invention, a highly-pure fluoroaryl borane derivative containing no impurities, such as coloring components, can be manufactured readily and efficiently. In addition, because the fluoroaryl borane derivative obtained by the above manufacturing method contains no impurities, such as coloring components, it can be an useful compound used as a cocatalyst for a metallocene catalyst (polymerization catalyst) utilized in a cation complex polymerization reaction or a catalyst for silicone photopolymerization.

The following will explain in detail the present invention by way of Examples and Comparative Examples without any intention to limit the scope thereof.

EXAMPLE 1

Air inside a reaction vessel equipped with a thermometer, a dropping funnel, a stirrer, a nitrogen gas conduit, and a reflux condenser was replaced with a nitrogen gas in a satisfactory manner. Then, 300 ml of a diethyl ether (chain ether solvent) solution containing 0.765 mol of methyl magnesium bromide as the hydrocarbon magnesium halide (2) was charged to the reaction vessel. Meanwhile, 0.729 mol of bromopentafluorobenzene is charged to the dropping funnel as the fluoroaryl halide.

Then, bromopentafluorobenzene in the dropping funnel was dropped to the reaction vessel over 90 minutes at room temperature, and the reaction solution was stirred for 30 minutes at room temperature. Consequently, pentafluorophenyl magnesium bromide as the fluoroaryl magnesium halide was obtained in the form of a colorless diethyl ether solution.

The yield of the pentafluorophenyl magnesium bromide produced by the above reaction was measured by means of $^{19}$F-NMR (Nuclear Magnetic Resonance). To be more specific, $^{19}$F-NMR was measured using p-fluorotoluene as an internal standard reagent. In this measuring, trifluoroacetic acid was used as the standard material, and its signal position was set as 0 ppm. Then, a peak integral of a fluorine atom of p-fluorotoluene, and a peak integral of fluorine atoms at the ortho-position of a pentafluorophenyl group in pentafluorophenyl magnesium bromide were calculated from the resulting $^{19}$F-NMR chart first, and thence an amount of pentafluorophenyl magnesium bromide was calculated using the above two peak integrals. Consequently, the yield of pentafluorophenyl magnesium bromide thus found was 93.5 mol % based on bromopentafluorobenzene.

EXAMPLE 2

Air inside a reaction vessel of the same type as the one used in Example 1 was replaced with a nitrogen gas in a satisfactory manner, after which 300 ml of diethyl ether solution containing 0.729 mol of ethyl magnesium bromide as the hydrocarbon magnesium halide (2) was charged to the reaction vessel. Meanwhile, 0.729 mol of bromopentafluorobenzene was charged to the dropping funnel.

Then, bromopentafluorobenzene was dropped to the reaction vessel over 90 minutes at room temperature, and the reaction solution was stirred for 30 minutes at room temperature. Consequently, pentafluorophenyl magnesium bromide was obtained in the form of a colorless diethyl ether solution. The yield of pentafluorophenyl magnesium bromide measured in the same manner as Example 1 was 95.0 mol % based on bromopentafluorobenzene.

EXAMPLE 3

Air inside a reaction vessel of the same type as the one used in Example 1 was replaced with a nitrogen gas in a satisfactory manner, after which 100 ml of diethyl ether solution containing 0.197 mol of n-propyl magnesium bromide as the hydrocarbon magnesium halide (2) was charged to the reaction vessel. Meanwhile, 0.182 mol of bromopentafluorobenzene was charged to the dropping funnel.

Then, bromopentafluorobenzene in the dropping funnel was dropped to the reaction vessel over 2 hours at room temperature, and the reaction solution was stirred for 30 minutes at room temperature. Consequently, pentafluorophenyl magnesium bromide was obtained in the form of a colorless diethyl ether solution. The yield of pentafluorophenyl magnesium bromide measured in the same manner as Example 1 was 92.2 mol % based on bromopentafluorobenzene.

EXAMPLE 4

Air inside a reaction vessel of the same type as the one used in Example 1 was replaced with a nitrogen gas in a satisfactory manner, after which 22 ml of a t-butylmethyl ether (chain ether solvent) solution containing 0.0214 mol of suspended n-propyl magnesium bromide was charged to the reaction vessel. Meanwhile, 0.0184 mol of bromopentafluorobenzene was charged to the dropping funnel.

Then, bromopentafluorobenzene in the dropping funnel was dropped to the reaction vessel over 45 minutes at room temperature, and the reaction solution was stirred for 3 hours at room temperature. Consequently, pentafluorophenyl magnesium bromide was obtained in the form of colorless t-butylmethyl ether solution.

The yield of pentafluoropheyl magnesium bromide produced in the above reaction was measured in the following manner. That is, pentafluorophenyl magnesium bromide was converted to iodopentafluorobenzene by adding dropwise a t-butylmethyl ether solution containing 0.025 mol of iodine to the obtained reaction solution. An amount of iodopentafluorobenzene thus produced was determined by means of gas chromatography. Consequently, the yield of pentafluorophenyl magnesium bromide thus measured was 95.4 mol % based on bromopentafluorobenzene.

EXAMPLE 5

Air inside a reaction vessel of the same type as the one used in Example 1 was replaced with a nitrogen gas in a satisfactory manner, after which 130 ml of a t-butyl methyl ether (chain ether solvent) solution containing 0.198 mol of suspended ethyl magnesium bromide as the hydrocarbon magnesium halide (2) was charged to the reaction vessel. Meanwhile, 0.182 mol of bromopentafluorobenzene was charged to the dropping funnel. Then, bromopentafluorobenzene in the dropping funnel was dropped to the reaction vessel over 45 minutes at room temperature, and the reaction solution was stirred for 4 hours at room temperature. Consequently, pentafluorophenyl magnesium bromide was obtained in the form of a colorless t-butylmethyl ether solution. The yield of pentafluorophenyl magnesium bromide measured in the same manner as Example 1 was 98.0 mol % based on bromopentafluorobenzene.

EXAMPLE 6

Air inside a reaction vessel of the same type as the one used in Example 1 was replaced with a nitrogen gas in a satisfactory manner, after which 60 ml of a 1,2-dimethoxy ethane (chain ether solvent) solution containing 0.088 mol of suspended ethyl magnesium bromide was charged to the reaction vessel. Meanwhile, 0.081 mol of bromopentafluorobenzene was charged to the dropping funnel. Further, 0.5 g of methyl iodide was charged to the reaction vessel through a micro-syringe, and the reaction solution was stirred for 10 minutes at room temperature. Then, bromopentafluorobenzene in the dropping funnel was dropped to the reaction vessel over 45 minutes at room temperature, and the reaction solution was stirred for 4 hours at room temperature. Consequently, pentafluorophenyl magnesium bromide was obtained in the form of a colorless 1,2-dimethoxy ethane solution. The yield of pentafluorophenyl magnesium bromide measured in the same manner as Example 1 was 98.5 mol % based on bromopentafluorobenzene.

EXAMPLE 7

Air inside a reaction vessel of the same type as the one used in Example 1 was replaced with a nitrogen gas in a satisfactory manner, after which 100 ml of a diisopropyl ether (chain ether solvent) solution containing 0.197 mol of suspended n-propyl magnesium bromide was charged to the reaction vessel. Meanwhile, 0.182 mol of bromopentafluorobenzene was charged to the dropping funnel.

Then, bromopentafluorobenzene in the dropping funnel was dropped to the reaction vessel over 10 minutes at room temperature, and the reaction solution was stirred for 5 hours at 50° C. Consequently, pentafluorophenyl magnesium bromide was obtained in the form of a colorless diisopropyl ether solution. The yield of pentafluorophenyl magnesium bromide measured in the same manner as Example 4 was 90.9 mol % based on bromopentafluorobenzene.

EXAMPLE 8

Air inside a reaction vessel of the same type as the one used in Example 1 was replaced with a nitrogen gas in a satisfactory manner, after which 70 ml of a diisopropyl ether (chain ether solvent) solution containing 0.066 mol of suspended ethyl magnesium bromide was charged to the reaction vessel. Meanwhile, 0.060 mol of bromopentafluorobenzene and 20 ml of diisopropyl ether (chain ether solvent) were charged to the dropping funnel. Then, the diisopropyl ether solution of bromopentafluorobenzene in the dropping funnel was dropped to the reaction vessel over 2 hours at room temperature, and the reaction solution was stirred for 12 hours at room temperature. Consequently, pentafluorophenyl magnesium bromide was obtained in the form of a colorless diisopropyl ether solution. The yield of pentafluorophenyl magnesium bromide measured in the same manner as Example 1 was 94.3 mol % based on bromopentafluorobenzene.

EXAMPLE 9

Air inside a reaction vessel of the same type as the one used in Example 1 was replaced with a nitrogen gas in a satisfactory manner, after which 50 ml of a dipropyl ether (chain ether solvent) solution containing 0.065 mol of ethyl magnesium bromide was charged to the reaction vessel. Meanwhile, 0.060 mol of bromopentafluorobenzene and 20 ml of dipropyl ether (chain ether solvent) were charged to the dropping funnel. Then, the dipropyl ether solution of bromopentafluorobenzene in the dropping funnel was dropped to the reaction vessel over 1 hour at room temperature, and the reaction solution was stirred for 2 hours at room temperature. Consequently, pentafluorophenyl magnesium bromide was obtained in the form of a colorless dipropyl ether solution. The yield of pentafluorophenyl magnesium bromide measured in the same manner as Example 1 was 94.6 mol % based on bromopentafluorobenzene.

EXAMPLE 10

Air inside a reaction vessel of the same type as the one used in Example 1 was replaced with a nitrogen gas in a satisfactory manner, after which 90 ml of a dibutyl ether (chain ether solvent) solution containing 0.188 mol of isopropyl magnesium bromide as the hydrocarbon magnesium halide (2) was charged to the reaction vessel. Meanwhile, 0.182 mol of bromopentafluorobenzene and 50 ml of dibutyl ether (chain ether solvent) were charged to the dropping funnel. Then, the dibutyl ether solution of bromopentafluorobenzene in the dropping funnel was dropped to the reaction vessel over 2 hours at room temperature, and the reaction solution was stirred for 2 hours at 35° C. Consequently, pentafluorophenyl magnesium bromide was obtained in the form of a light-yellow dibutyl ether solution. The yield of pentafluorophenyl magnesium bromide measured in the same manner as Example 1 was 97.5 mol % based on bromopentafluorobenzene.

EXAMPLE 11

Air inside a reaction vessel of the same type as the one used in Example 1 was replaced with a nitrogen gas in a satisfactory manner, after which 9 ml of a diethyl ether solution containing 0.0195 mol of phenyl magnesium bromide as the hydrocarbon magnesium halide (2) was charged to the reaction vessel. Meanwhile, 0.0184 mol of bromopentafluorobenzene was charged to the dropping funnel.

Then, bromopentafluorobenzene in the dropping funnel was dropped to the reaction vessel over 5 minutes at room temperature, and the reaction solution was stirred for 2.5 hours at room temperature. Consequently, pentafluorophenyl magnesium bromide was obtained in the form of a colorless diethyl ether solution. The yield of pentafluorophenyl magnesium bromide measured in the same manner as Example 4 was 78.0 mol % based on bromopentafluorobenzene.

EXAMPLE 12

Air inside a reaction vessel of the same type as the one used in Example 1 was replaced with a nitrogen gas in a satisfactory manner, after which 20 ml of a diethyl ether solution containing 0.0188 mol of cyclohexyl magnesium bromide as the hydrocarbon magnesium halide (2) was charged to the reaction vessel. Meanwhile, 0.0186 mol of bromopentafluorobenzene was charged to the dropping funnel.

Then, bromopentafluorobenzene in the dropping funnel was dropped to the reaction vessel over 5 minutes at room temperature, and the reaction solution was stirred for 2 hours at room temperature. Consequently, pentafluorophenyl magnesium bromide was obtained in the form of a colorless diethyl ether solution. The yield of pentafluorophenyl magnesium bromide measured in the same manner as Example 1 was 88.5 mol % based on bromopentafluorobenzene.

EXAMPLE 13

Air inside a reaction vessel of the same type as the one used in Example 1 was replaced with a nitrogen gas in a satisfactory manner, after which 20 ml of a diethyl ether solution containing 0.0180 mol of ethyl magnesium bromide was charged to the reaction vessel. Meanwhile, 0.017 mol of iodopentafluorobenzene was charged to the dropping funnel as the fluoroaryl halide.

Then, iodopentafluorobenzene in the dropping funnel was dropped to the reaction vessel over 30 minutes at room temperature, and the reaction solution was stirred for 2 hours at room temperature. Consequently, pentafluorophenyl magnesium bromide was obtained in the form of a colorless diethyl ether solution. The yield of pentafluorophenyl magnesium bromide measured in the same manner as Example 1 was 92.1 mol % based on iodopentafluorobenzene.

EXAMPLE 14

Air inside a reaction vessel of the same type as the one used in Example 1 was replaced with a nitrogen gas in a satisfactory manner, after which 30 ml of a toluene solution containing 0.016 mol of bromopentafluorobenzene was charged to the reaction vessel. Meanwhile, 10 ml of diethyl ether solution containing 0.0180 mol of ethyl magnesium bromide was charged to the dropping funnel.

Then, ethyl magnesium bromide in the dropping funnel was dropped to the reaction vessel over 30 minutes at room temperature, and the reaction solution was stirred for 2 hours at room temperature. Consequently, pentafluorophenyl magnesium bromide was obtained in the form of a colorless toluene - diethyl ether mixed solution. The yield of pentafluorophenyl magnesium bromide measured in the same manner as Example 1 was 91.9 mol % based on bromopentafluorobenzene.

EXAMPLE 15

Air inside a reaction vessel of the same type as the one used in Example 1 was replaced with a nitrogen gas in a satisfactory manner, after which 20 ml of a t-butyl methyl ether solution containing 0.0199 mol of suspended n-propyl magnesium bromide was charged to the reaction vessel. Meanwhile, 0.0183 mol of 1-bromo-2,3,5,6-tetrafluorobenzene was charged to the dropping funnel as the fluoroaryl halide.

Then, 1-bromo-2,3,5,6-tetrafluorobenzene in the dropping funnel was dropped to the reaction vessel over 20 minutes at room temperature, and the reaction solution was stirred for 4 hours at room temperature. Consequently, 2,3,5,6-tetrafluorophenyl magnesium bromide was obtained in the form of a colorless t-butyl methyl ether solution. The yield of 2,3,5,6-tetrafluorophenyl magnesium bromide measured in the same manner as Example 1 was 85.2 mol % based on 1-bromo-2,3,5,6-tetrafluorobenzene.

EXAMPLE 16

Air inside a reaction vessel of the same type as the one used in Example 1 was replaced with a nitrogen gas in a satisfactory manner, after which 9 ml of a diethyl ether solution containing 0.020 mol of n-propyl magnesium bromide was charged to the reaction vessel. Meanwhile, 0.020 mol of 1-bromo-2,4,6-trifluorobenzene was charged to the dropping funnel as the fluoroaryl halide.

Then, 1-bromo-2,4,6-trifluorobenzene in the dropping funnel was dropped to the reaction vessel over 15 minutes at room temperature, and the reaction solution was stirred for 2 hours at room temperature. Consequently, 2,4,6-trifluorophenyl magnesium bromide was obtained in the form of a colorless diethyl ether solution. The yield of 2,4,6-trifluorophenyl magnesium bromide measured in the same manner as Example 1 was 55.5 mol % based on 1-bromo-2,4,6-trifluorobenzene.

COMPARATIVE EXAMPLE 1

Air inside a reaction vessel of the same type as the one used in Example 1 was replaced with a nitrogen gas in a satisfactory manner, after which 30 ml of a diethyl ether solution containing 0.066 mol of ethyl magnesium bromide was charged to the reaction vessel. Meanwhile, 0.060 mol of chloropentafluorobenzene was charged to the dropping funnel.

Then, chloropentafluorobenzene in the dropping funnel was dropped to the reaction vessel over 15 minutes at room temperature. The reaction solution was refluxed (37° C.) for 8 hours, and stirred for 10 hours at room temperature. Consequently, pentafluorophenyl magnesium bromide was obtained in the form of a diethyl ether solution. The yield of pentafluorophenyl magnesium bromide measured in the same manner as Example 1 was 21.6 mol % based on chloropentafluorobenzene.

COMPARATIVE EXAMPLE 2

Air inside a reaction vessel of the same type as the one used in Example 1 was replaced with a nitrogen gas in a satisfactory manner, after which 20 ml of a t-butyl methyl ether containing 0.0201 mol of suspended n-propyl magnesium bromide was charged to the reaction vessel. Meanwhile, 0.0182 mol of 1-bromo-4-fluorobenzene was charged to the dropping funnel.

Then, 1-bromo-4-fluorobenzene in the dropping funnel was dropped to the reaction vessel over 10 minutes at room temperature. The reaction solution was heated to 56° C., and stirred for 2 hours. The resulting reaction solution was analyzed in the same manner as Example 1, but 4-fluorophenyl magnesium bromide was not contained therein. In short, n-propyl magnesium bromide and 1-bromo-4-fluorobenzene did not react with each other.

COMPARATIVE EXAMPLE 3

Air inside a reaction vessel of the same type as the one used in Example 1 was replaced with a nitrogen gas in a satisfactory manner, after which 20 ml of a diethyl ether solution containing 0.0201 mol of n-propyl magnesium bromide was charged to the reaction vessel. Meanwhile, 0.0182 mol of 1-bromo-2,6-difluorobenzene was charged to the dropping funnel.

Then, 1-bromo-2,6-difluorobenzene in the dropping funnel was dropped to the reaction vessel over 10 minutes at room temperature. The reaction solution was heated to 40° C., and stirred for 2 hours. The resulting reaction solution was analyzed in the same manner as Example 1, but 2,6-difluorophenyl magnesium bromide was not contained therein. In short, n-propyl magnesium bromide and 1-bromo-2,6-difluorobenzene did not react with each other.

COMPARATIVE EXAMPLE 4

Air inside a reaction vessel of the same type as the one used in Example 1 was replaced with a nitrogen gas in a satisfactory manner, after which 0.051 mol of magnesium and 65 ml of dibutyl ether were charged to the reaction vessel, and cooled to 5° C. Meanwhile, 0.050 mol of bromopentafluorobenzene was charged to the dropping funnel. Further, 0.33 g (0.003 mol: 6.1 mol % with respect to bromopentafluorobenzene) of ethyl bromide was added to the reaction vessel, and the reaction solution was stirred for 1 hour at room temperature. Then, bromopentafluorobenzene in the dropping funnel was dropped to the reaction vessel over 1 hour at 40° C., and the reaction solution was let undergo a reaction for 1 hour at 40° C. Then, the reaction solution was cooled to room temperature, and the yield of pentafluorophenyl magnesium bromide measured in the same manner as Example 1 was 5.6 mol % based on bromopentafluorobenzene.

EXAMPLE 17

Air inside a reaction vessel of the same type as the one used in Example 1 was replaced with a nitrogen gas in a satisfactory manner, after which 70 ml of diethyl ether solution containing 0.056 mol of boron trifluoride ethyl ether complex as the boron compound was charged to the reaction vessel. Meanwhile, 120 ml of diethyl ether solution containing 0.168 mol of pentafluorophenyl magnesium bromide obtained as the fluoroaryl magnesium halide in Example 3 was charged to the dropping funnel.

Then, the diethyl ether solution in the dropping funnel was dropped to the reaction vessel over 1 hour at room temperature with the stirring of the diethyl ether solution therein. Then, the reaction solution was heated and refluxed for 4 hours, after which the reaction solution was cooled to room temperature. Consequently, tris(pentafluorophenyl) borane as the tris(fluoroaryl)borane was obtained in the form of a colorless diethyl ether solution.

The yield of tris(pentafluorophenyl)borane measured in the same manner as Example 1 was 93.6 mol % based on pentafluorophenyl magnesium bromide.

EXAMPLE 18

Air inside a reaction vessel of the same type as the one used in Example 1 was replaced with a nitrogen gas in a satisfactory manner, after which 20 ml of a diisopropyl ether solution containing 0.017 mol of boron trifluoride ethyl ether complex as the boron compound was charged to the reaction vessel. Meanwhile, 100 ml of diisopropyl ether solution containing 0.057 mol of suspended pentafluorophenyl magnesium bromide obtained as the fluoroaryl magnesium halide in Example 6 was charged to the dropping funnel. Then, the diisopropyl ether solution in the dropping funnel was dropped to the reaction vessel over 1 hour at room temperature with the stirring of the diisopropyl ether solution in the reaction vessel. Then, the reaction solution was let undergo a reaction (maturation) for 2 hours at 35° C., and cooled to room temperature. Consequently, tris (pentafluorophenyl)borane was obtained in the form of a colorless diisopropyl ether solution.

The yield of tris(pentafluorophenyl)borane measured in the same manner as Example 1 was 57.1 mol % based on pentafluorophenyl magnesium bromide.

EXAMPLE 19

Air inside a reaction vessel of the same type as the one used in Example 1 was replaced with a nitrogen gas in a satisfactory manner, after which 20 ml of a diisopropyl ether solution containing 0.019 mol of boron trifluoride ethyl ether complex as the boron compound, and 0.060 mol of diethyl ether were charged to the reaction vessel. Meanwhile, 100 ml of diisopropyl ether solution containing 0.057 mol of suspended pentafluorophenyl magnesium bromide obtained as the fluoroaryl magnesium halide in Example 8 was charged to the dropping funnel. Then, the diisopropyl ether solution in the dropping funnel was dropped to the reaction vessel over 1 hour at room temperature with the stirring of the diisopropyl ether solution in the reaction vessel. Then, the reaction solution was let undergo a reaction (maturation) for 2 hours at 35° C., and then cooled to room temperature. Consequently, tris(pentafluorophenyl) borane was obtained in the form of a colorless diisopropyl ether solution.

The yield of tris(pentafluorophenyl)borane measured in the same manner as Example 1 was 93.3 mol % based on pentafluorophenyl magnesium bromide.

EXAMPLE 20

After pentafluorophenyl magnesium bromide was obtained in Example 2, the following reaction was conducted continuously (in 1-pot reaction). That is, air inside the reaction vessel used in Example 2 was replaced with a nitrogen gas in a satisfactory manner. At this point, 400 ml of a diethyl ether solution containing 0.692 mole of pentafluorophenyl magnesium bromide was in the reaction vessel. Meanwhile, 0.173 mol of boron trifluoride ethyl ether complex was charged to the dropping funnel.

Then, the boron trifluoride ethyl ether complex in the dropping funnel was dropped to the reaction vessel over 1.5 hour at room temperature, and 280 ml of dibutyl ether (chain ether solvent) was added to the reaction solution through the dropping funnel. Then, the reaction solution was heated to 130° C. to proceed the same reaction (maturation), while diethyl ether and ethyl bromide produced as a by-product when synthesizing pentafluorophenyl magnesium bromide were distilled out under normal pressure. Then, the reaction solution was cooled to room temperature. Consequently, tetrakis(pentafluorophenyl)borate.magnesium bromide as the tetrakis(fluoroaryl)borate.magnesium compound was obtained in the form of a colorless dibutyl ether solution.

The yield of tetrakis(pentafluorophenyl) borate.magnesium bromide measured in the same manner as Example 1 was 91.5 mol % based on pentafluorophenyl magnesium bromide.

EXAMPLE 21

After pentafluorophenyl magnesium bromide was obtained in Example 10, the following reaction was conducted continuously (in 1-pot reaction). That is, 170 ml of a dibutyl ether solution containing 0.177 mol of pentafluorophenyl magnesium bromide was in the reaction vessel used in Example 10. Meanwhile, 0.045 mol of boron trifluoride ethyl ether complex was charged to the dropping funnel. Further, the reflux condenser was replaced with a distilling apparatus.

Then, boron trifluoride ethyl ether complex in the dropping funnel was dropped to the reaction vessel over 1 hour at room temperature with the stirring of the dibutyl ether solution in the reaction vessel. Then, the reaction solution was heated to 100° C. (maturation) for 2 hours, while isopropyl bromide produced as a by-product when synthesizing pentafluorophenyl magnesium bromide was distilled out. Then, the reaction solution was cooled to room temperature. Consequently, tetrakis(pentafluorophenyl) borate-.magnesium bromide was obtained in the form of a colorless dibutyl ether solution. The yield of tetrakis (pentafluorophenyl)borate.magnesium bromide measured in the same manner as Example 1 was 90.2 mol % based on pentafluorophenyl magnesium bromide.

EXAMPLE 22

Air inside a reaction vessel of the same type as the one used in Example 1 was replaced with a nitrogen gas in a satisfactory manner, after which 20 ml of a diethyl ether solution containing 0.010 mol of p-fluorophenyl magnesium bromide as the hydrocarbon magnesium halide (7) was charged to the reaction vessel. Meanwhile, 16 ml of diethyl ether solution containing 0.010 mol of tris (pentafluorophenyl)borane obtained as tris(fluoroaryl) borane in Example 17 was charged to the dropping funnel.

Then, the diethyl ether solution in the dropping funnel was dropped to the reaction vessel over 5 minutes at room temperature with the stirring of the diethyl ether solution in the reaction vessel. Then, the reaction solution was heated to 50° C., and stirred for 3 hours, after which the reaction solution was cooled to room temperature. Consequently, p-fluorophenyl-tris(pentafluorophenyl)borate.magnesium bromide as the fluoroaryl borate.magnesium halide derivative was obtained in the form of a colorless diethyl ether solution.

The yield of p-fluorophenyl-tris(pentafluorophenyl) borate.magnesium bromide measured in the same manner as Example 1 was 86.3 mol % based on p-fluorophenyl magnesium bromide.

COMPARATIVE EXAMPLE 5

Air inside a reaction vessel of the same type as the one used in Example 1 was replaced with a nitrogen gas in a satisfactory manner, after which 0.188 mol of magnesium and 65 g of diethyl ether were charged to the reaction vessel. Meanwhile, 0.182 mol of bromopentafluorobenzene was charged to the dropping funnel. Then, bromopentafluorobenzene in the dropping funnel was dropped to the reaction vessel over 3 hours at room temperature with the stirring of diethyl ether in the reaction vessel, and the reaction solution was heated to the refluxing temperature (39° C.) for 2 hours (maturation). Consequently, pentafluorophenyl magnesium bromide was obtained in the form of a black diethyl ether solution. The yield of pentafluorophenyl magnesium bromide measured in the same manner as Example 1 was 97.5 mol % based on bromopentafluorobenzene.

Air inside the reaction vessel of the same type as the one used in Example 1 was replaced with a nitrogen gas in a satisfactory manner, after which 0.060 mol of boron trifluoride ethyl ether complex and 48 g of diethyl ether were charged to the reaction vessel. Meanwhile, the diethyl ether solution of pentafluorophenyl magnesium bromide obtained above was charged to the dropping funnel. Then, the diethyl ether solution of pentafluorophenyl magnesium bromide in the dropping funnel was dropped to the reaction vessel over 1 hour at room temperature with the stirring of diethyl ether in the reaction vessel. Then, the reaction solution was heated to 35° C. for 2 hours (maturation), and then cooled to room temperature. The yield of tris(pentafluorophenyl)borane measured in the same manner as Example 1 was 87.6 mol % based on bromopentafluorobenzene. However, the resulting diethyl ether solution of tris(pentafluorophenyl)borane was black.

COMPARATIVE EXAMPLE 6

Air inside a reaction vessel of the same type as the one used in Example 1 was replaced with a nitrogen gas in a satisfactory manner, after which 50 ml of a tetrahydrofuran solution containing 0.018 mol of ethyl magnesium bromide was charged to the reaction vessel. Meanwhile, 0.018 mol of bromopentafluorobenzene was charged to the dropping funnel. Then, bromopentafluorobenzene in the dropping funnel was dropped to the reaction vessel over 10 minutes at room temperature with the stirring of the tetrahydrofuran solution in the reaction vessel, and the reaction solution was heated to 35° C. for 1 hour. Consequently, pentafluorophenyl magnesium bromide was obtained in the form of a light yellow tetrahydrofuran solution. The yield of pentafluorophenyl magnesium bromide measured in the same manner as Example 1 was 93.9 mol % based on bromopentafluorobenzene.

Air inside the reaction vessel of the same type as the one used in Example 1 was replaced with a nitrogen gas in a satisfactory manner, after which 0.0056 mol of a boron trifluoride tetrahydrofuran complex and 50 ml of tetrahydrofuran were charged to the reaction vessel. Meanwhile, the tetrahydrofuran solution of pentafluorophenyl magnesium bromide obtained above was charged to the dropping funnel. Then, the tetrahydrofuran solution of pentafluorophenyl magnesium bromide in the dropping funnel was dropped to the reaction vessel over 1 hour at room temperature with the stirring of tetrahydrofuran in the reaction vessel. Then, the reaction solution was stirred for 2 hours (maturation) at 35° C., and then cooled to room temperature. The yield of tris(pentafluorophenyl)borane measured in the same manner as Example 1 was 35.4 mol % based on bromopentafluorobenzene. The resulting tetrahydrofuran-diethyl ether mixed solution of tris(pentafluorophenyl)borane was light yellow and contained many by-products.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for manufacturing fluoroaryl magnesium halide expressed by General Formula (1):

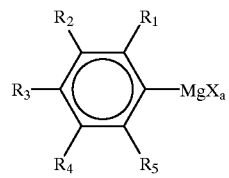

(1)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_a$ represents one of a chlorine atom, a bromine atom, and an iodine atom;

by reacting, in a solvent containing a chain ether solvent, hydrocarbon magnesium halide expressed by General Formula (2):

$R_6MgX_a$ (2)

where $R_6$ represents a hydrocarbon group, and $X_a$ represents one of a chlorine atom, a bromine atom, and an iodine atom;

with fluoroaryl halide expressed by General Formula (3):

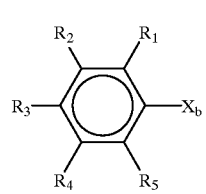

(3)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_b$ represents one of a bromine atom and an iodine atom.

2. A method for manufacturing tris(fluoroaryl)borane comprising:

step (A) of manufacturing fluoroaryl magnesium halide expressed by General Formula (1):

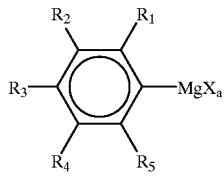

(1)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_a$ represents one of a chlorine atom, a bromine atom, and an iodine atom;

by reacting, in a solvent containing a chain ether solvent, hydrocarbon magnesium halide expressed by General Formula (2):

$R_6MgX_a$ (2)

where $R_6$ represents a hydrocarbon group, and $X_a$ represents one of a chlorine atom, a bromine atom, and an iodine atom;

with fluoroaryl halide expressed by General Formula (3):

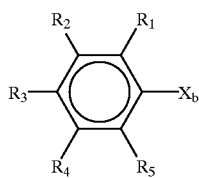

(3)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_b$ represents one of a bromine atom and an iodine atom; and step (B) of manufacturing tris(fluoroaryl)borane expressed by General Formula (5):

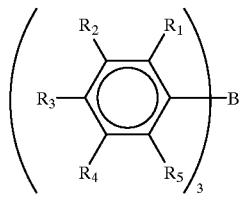

(5)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms;

by reacting the fluoroaryl magnesium halide expressed by General Formula (1) and obtained in the step (A) with a boron compound expressed by General Formula (4):

$B(X_c)_3$ (4)

where $X_c$ represents one of a fluorine atom, a chlorine atom, a bromine atom, an iodine atom, and an alkylalkoxy group.

3. A method for manufacturing a tetrakis(fluoroaryl)borate.magnesium compound comprising:

step (A) of manufacturing fluoroaryl magnesium halide expressed by General Formula (1):

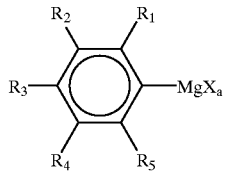

(1)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_a$ represents one of a chlorine atom, a bromine atom, and an iodine atom;

by reacting, in a solvent containing a chain ether solvent, hydrocarbon magnesium halide expressed by General Formula (2):

$R_6MgX_a$ (2)

where $R_6$ represents a hydrocarbon group, and $X_a$ represents one of a chlorine atom, a bromine atom, and an iodine atom;

with fluoroaryl halide expressed by General Formula (3):

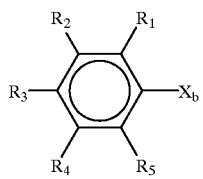

(3)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_b$ represents one of a bromine atom and an iodine atom; and step (B) of manufacturing a tetrakis(fluoroaryl)borate.magnesium compound expressed by General Formula (6):

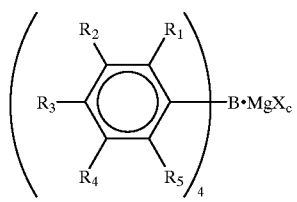

(6)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_c$ represents one of a fluorine atom, a chlorine atom, a bromine atom, an iodine atom, and an alkylalkoxy group;

by reacting the fluoroaryl magnesium halide expressed by General Formula (1) and obtained in the step (A) with a boron compound expressed by General Formula (4):

  (4)

where $X_c$ represents one of a fluorine atom, a chlorine atom, a bromine atom, an iodine atom, and an alkylalkoxy group.

4. A method for manufacturing a fluoroaryl borate.magnesium halide derivative comprising:

step (A) of manufacturing fluoroaryl magnesium halide expressed by General Formula (1):

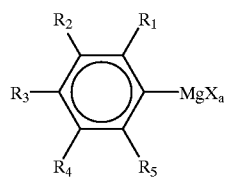  (1)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_a$ represents one of a chlorine atom, a bromine atom, and an iodine atom;

by reacting, in a solvent containing a chain ether solvent, hydrocarbon magnesium halide expressed by General Formula (2):

  (2)

where $R_6$ represents a hydrocarbon group, and $X_a$ represents one of a chlorine atom, a bromine atom, and an iodine atom;

with fluoroaryl halide expressed by General Formula (3):

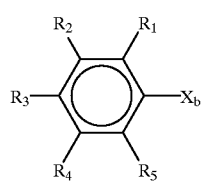  (3)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, and $X_b$ represents one of a bromine atom and an iodine atom;

step (B) of manufacturing tris(fluoroaryl)borane expressed by General Formula (5):

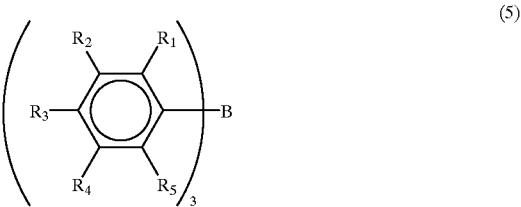  (5)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms;

by reacting the fluoroaryl magnesium halide expressed by General Formula (1) and obtained in the step (A) with a boron compound expressed by General Formula (4):

  (4)

where $X_c$ represents one of a fluorine atom, a chlorine atom, a bromine atom, an iodine atom, and an alkylalkoxy group; and step (C) of manufacturing a fluoroaryl borate.magnesium halide derivative expressed by General Formula (8):

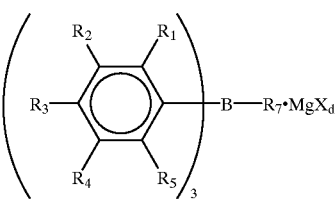  (8)

where each of $R_1$, $R_2$, $R_3$, $R_4$, and $R_5$ independently represents one of a hydrogen atom, a fluorine atom, a hydrocarbon group, and an alkoxy group, provided that at least three of $R_1$–$R_5$ are fluorine atoms, $R_7$ represents a hydrocarbon atom, and $X_d$ represents one of a chlorine atom, a bromine atom, and an iodine atom;

by reacting the tris(fluoroaryl)borane expressed by General Formula (5) and obtained in the step (B) with hydrocarbon magnesium halide expressed by General Formula (7):

  (7)

where $R_7$ represents a hydrocarbon group, and $X_d$ represents one of a chlorine atom, a bromine atom, and an iodine atom.

5. The method for manufacturing fluoroaryl magnesium halide of claim 1, wherein a ratio of the hydrocarbon magnesium halide expressed by General Formula (2) to the fluoroaryl halide expressed by General Formula (3) is in a range between 0.8 and 2.0 equivalent.

6. The method for manufacturing tris(fluoroaryl)borane of claim 2, wherein a mole ratio of the boron compound expressed by General Formula (4) to the fluoroaryl magnesium halide expressed by General Formula (1) is in a range between 2.0 and 3.4.

7. The method for manufacturing a tetrakis(fluoroaryl) borate.magnesium compound of claim 3, wherein a mole ratio of the boron compound expressed by General Formula (4) to the fluoroaryl magnesium halide expressed by General Formula (1) is in a range between 3.5 and 5.0.

8. The method for manufacturing tris(fluoroaryl)borane of claim 2, wherein the fluoroaryl magnesium halide expressed by General Formula (1) is reacted with the boron compound expressed by General Formula (4) in the presence of 0.5–3.0 equivalents of diethyl ether with respect to the fluoroaryl magnesium halide expressed by General Formula (1).

9. The method for manufacturing a tetrakis(fluoroaryl)borate.magnesium compound of claim 3, wherein the fluoroaryl magnesium halide expressed by General Formula (1) is reacted with the boron compound expressed by General Formula (4) in the presence of 0.5–3.0 equivalents of diethyl ether with respect to the fluoroaryl magnesium halide expressed by General Formula (1) .

10. The method for manufacturing a fluoroaryl borate.magnesium halide derivative of claim 4, wherein the tris(fluoroaryl)borane expressed by General Formula (5) is reacted with the hydrocarbon magnesium halide expressed by General Formula (7) in the presence of 0.5–3.0 equivalents of diethyl ether with respect to the tris(fluoroaryl)borane expressed by General Formula (5).

11. The method for manufacturing fluoroaryl magnesium halide of claim 1, wherein the solvent is a solvent containing a chain ether solvent except for diethyl ether.

12. The method for manufacturing tris(fluoroaryl)borane of claim 2, wherein the solvent is a solvent containing a chain ether solvent except for diethyl ether.

13. The method for manufacturing a tetrakis(fluoroaryl)borate.magnesium compound of claim 3, wherein the solvent is a solvent containing a chain ether solvent except for diethyl ether.

14. The method for manufacturing a fluoroaryl borate.magnesium halide derivative of claim 4, wherein the solvent is a solvent containing a chain ether solvent except for diethyl ether.

15. The method for manufacturing tris(fluoroaryl)borane of claim 2, wherein a mixing temperature of the fluoroaryl magnesium halide expressed by General Formula (1) with the boron compound expressed by General Formula (4) is in a range between −30° C. and 50° C.

16. The method for manufacturing tris(fluoroaryl)borane of claim 2, wherein a reaction temperature of the fluoroaryl magnesium halide expressed by General Formula (1) with the boron compound expressed by General Formula (4) is in a range between −20° C. and one of 150° C. and a refluxing temperature of the solvent, whichever is the lower, both inclusive.

17. The method for manufacturing a tetrakis(fluoroaryl)borate.magnesium compound of claim 3, wherein a reaction temperature of the fluoroaryl magnesium halide expressed by General Formula (1) with the boron compound expressed by General Formula (4) is in a range between 0° C. and one of 200° C. and a refluxing temperature of the solvent, whichever is the lower, both inclusive.

18. The method for manufacturing a fluoroaryl borate.magnesium halide derivative of claim 4, wherein a reaction temperature of the tris(fluoroaryl)borane expressed by General Formula (5) with the hydrocarbon magnesium halide expressed by General Formula (7) is in a range between −30° C. and a refluxing temperature of the solvent, both inclusive.

19. The method for manufacturing a fluoroaryl borate.magnesium halide derivative of claim 4, wherein a ratio of the hydrocarbon magnesium halide expressed by General Formula (7) to the tris(fluoroaryl)borane expressed by General Formula (5) is in a range between 0.5 and 5.0 equivalents both inclusive.

* * * * *